United States Patent
Panella et al.

(10) Patent No.: US 6,352,021 B1
(45) Date of Patent: Mar. 5, 2002

(54) APPARATUS FOR HEATING AND CONTROLLING THE PROCESS TEMPERATURE IN A TUNNEL PASTEURIZER

(75) Inventors: Graziano Panella, Grezzana; Giorgio Pasoli, Verona, both of (IT)

(73) Assignee: SASIB S.p.A., Parma (IT)

(*) Notice: Subject to any disclaimer, the term of this patent is extended or adjusted under 35 U.S.C. 154(b) by 0 days.

(21) Appl. No.: 09/907,622

(22) Filed: Jul. 19, 2001

(30) Foreign Application Priority Data

Aug. 9, 2000 (IT) .......................... VR00A0077

(51) Int. Cl.⁷ .............................. A23L 1/00; A23L 3/00; A61L 2/04
(52) U.S. Cl. .............................. 99/468; 99/330; 99/355; 99/361; 99/367; 99/371; 99/483; 99/470; 99/477
(58) Field of Search .................... 99/330, 467, 470, 99/468, 477, 483, 452–455, 361, 362, 367, 368, 370, 371, 352–355; 134/72, 131; 422/1, 26, 38, 292, 300, 307, 308; 426/401, 407, 521, 522

(56) References Cited

U.S. PATENT DOCUMENTS

| | | | | |
|---|---|---|---|---|
| 4,331,629 A | * | 5/1982 | Huling | 99/361 X |
| 4,441,406 A | * | 4/1984 | Becker et al. | 99/275 |
| 4,490,401 A | * | 12/1984 | Becker et al. | 426/407 |
| 4,693,902 A | * | 9/1987 | Richmond et al. | 99/483 X |
| 4,727,800 A | * | 3/1988 | Richmond et al. | 99/361 |
| 4,841,457 A | * | 6/1989 | Clyne et al. | 426/521 X |
| 5,750,174 A | * | 5/1998 | Lucassen | 99/470 X |
| 5,772,958 A | * | 6/1998 | Nielsen | 422/38 X |

* cited by examiner

Primary Examiner—Timothy F. Simone
(74) Attorney, Agent, or Firm—Browdy and Neimark

(57) ABSTRACT

An apparatus for heating and controlling the process temperature in a tunnel pasteurizer, in particular for packaged food products, in which the tunnel, provided with a conveyor able to advance the product, is substantially subdivided into a first pre-heating area, into a second pasteurization heat treatment area and a third area where the product is cooled. The apparatus is provided at least with a heat exchanger comprising a primary loop and a plurality of secondary loops, each of which is connected to the hydraulic loop of each sub-area. Each secondary loop is further provided with servo-controlled modulating valves which serve as means for controlling the temperature of the water of the sprinkler of each sub-area.

5 Claims, 3 Drawing Sheets

APPARATUS FOR HEATING AND CONTROLLING THE PROCESS TEMPERATURE IN A TUNNEL PASTEURIZER

BACKGROUND OF THE INVENTION

The present invention relates to an apparatus for heating and controlling the process temperature of a tunnel pasteurizer, in particular for packaged food products.

As is well known, pasteurization of packaged food products is the heat treatment whereto are subjected some types of products already packaged in final containers, in order to improve their preservation over time.

The type of pasteurization referred to hereinafter is "low temperature pasteurization" and with specific reference to food products constituted by drinks. This means that it takes place at a temperature lower than 90° C. by means of hot water which is sprayed in a programmed manner onto the containers in order to modify their temperature according to a defined thermal cycle.

The apparatus whereby the pasteurization process is achieved is essentially constituted by a tunnel through which is treated the product already packaged in the containers (bottles, cans or other containers) which are made to advance in the tunnel by means of a conveyor.

From the thermal point of view, the tunnel is essentially subdivided into three areas: a first area (area 1) for pre-heating, where the temperature of the product is increased to a value beyond which the actual heat treatment takes place; a second area (area 2) for heat treatment; a third area (area 3) for cooling, where the product is brought back roughly to ambient temperature in order to prevent undesired fermentation phenomena.

Each of these three area is further subdivided into two or more parts (sub-areas) in order to: (a) avoid thermal shocks and have the opportunity to recover heat between the heating and the cooling areas, or (b) have available areas at different temperatures, variable according to determined logic criteria, in the portion of the tunnel where the actual heat treatment takes place.

In accordance with the prior art, the heating of the water that is sprayed onto the product (process water) takes place by means of a plurality of heat exchangers, whereof each is associated to a sub-area of the areas 1, 2, 3 into which the tunnel is subdivided.

FIG. 3 shows a tunnel pasteurizer obtained according to the prior art in question (see also patent EP 960 574).

Each of said exchangers is formed by a single primary loop, whose fluid can be, depending on requirements, saturated steam, superheated water, hot water, etcetera, and by a single secondary loop wherein the process water circulates. Also present is a metering valve for the primary circuit and a condensation drain if the primary fluid is steam.

The process water circulates in each sub-area, through a hydraulic loop connecting the collection tank, located below the sprayed product, with sprinklers positioned above the product. The secondary loop of each heat exchanger is connected with the hydraulic loop of each sub-area, described above. To each sub-area of the pasteurizer, whose process water requires appropriate heating, must therefore be associated a specific heat exchanger.

While this constructive solution meets the operating requirements of the system very well, it does nonetheless have some drawbacks.

These are, essentially:

A relatively great complexity of the system for controlling and adjusting temperatures and hydraulic lines;

The need to provide for the maintenance of a high number of heat exchangers and of the equally numerous high pressure metering valves;

The inertia of the adjusting and controlling organs which are subject to continuous disposition variations;

The poor efficiency of the heat exchangers which are often called to operate in transient states.

To solve these series of drawbacks, some manufacturers have adopted a centralized heating system, which provides for the adoption of a single heat exchanger for all areas subjected to temperature control. This exchanger provides for heating a mass of water present inside a tank, which is maintained at sufficiently high temperature, and which is mixed with the process water of the various areas, in order to increase its temperature, depending on the need of each. Thermal energy is thus distributed by means of masses of hot water which are added in the areas where a temperature increase is required.

FIG. 2 schematically shows a tunnel pasteurizer obtained in accordance with this second type of prior art (see for instance patent WO 95/22352). This technical solution, while providing some unquestionable advantages over its prior art, still exhibits some drawbacks.

In particular:

High quantities of water masses inside the pasteurizer which must be heated before starting the conveyor (water masses present both in the process vats and in the common tank) with evident high energy expenditure;

Inevitable loss, at the final shut down of the pasteurizer, of the energy expended for the preventive heating of the water mass contained in the common tank;

Need for high water flow rates between the common tank and the various process vats if the temperature of the water in the common tank decreases (transferred power is equal to the product between water volume and temperature);

The existence of a single heat exchanger which, during the critical process control phases, must provide sufficient thermal energy both for the rapid heating of the areas of the pasteurizer, and for restoring the temperature of the water mass present in the common tank. And this with the eventuality that it may not be possible to perform the pasteurization process correctly and/or completely, with the consequent possible spoiling of the product;

The presence, inside the pasteurizer, of a great quantity of water at high temperature concentrated in a single area (the common tank) can alter, due to the heat exchange with the surrounding environment, the thermal equilibrium of the areas subject to temperature control;

The constant mixing of the water masses at different temperatures in the different areas of the pasteurizer requires the constant restoration of operating temperatures, once again with great energy expenditure.

SUMMARY OF THE INVENTION

The essential aim of the present invention therefore is to overcome the aforementioned drawbacks, relating to current systems for heating and controlling the process temperatures in tunnel pasteurizers, making available an apparatus that allows:

considerably to limit the number of heat exchangers used and the fluid regulating sets in their primary loop;

to limit the frequency of the variations in heat power supplied by the heat exchangers;

to maintain the process waters always separated from area to the other of the pasteurizer;

to avoid the use of a common tank containing large quantities of water at high temperature;

to simplify the structure of the hydraulic system of the pasteurizer.

These aims and others besides are all achieved by the subject apparatus for heating and controlling the process temperature, whose main characteristics are indicated in the claims that follow.

BRIEF DESCRIPTION OF THE DRAWINGS

Additional characteristics and advantages of the present invention shall become more readily apparent from the detailed description that follows of an embodiment of the apparatus in question illustrated, purely by way of non limiting example, in the accompanying drawings.

DESCRIPTION OF THE PREFERRED EMBODIMENT

Figure 1:
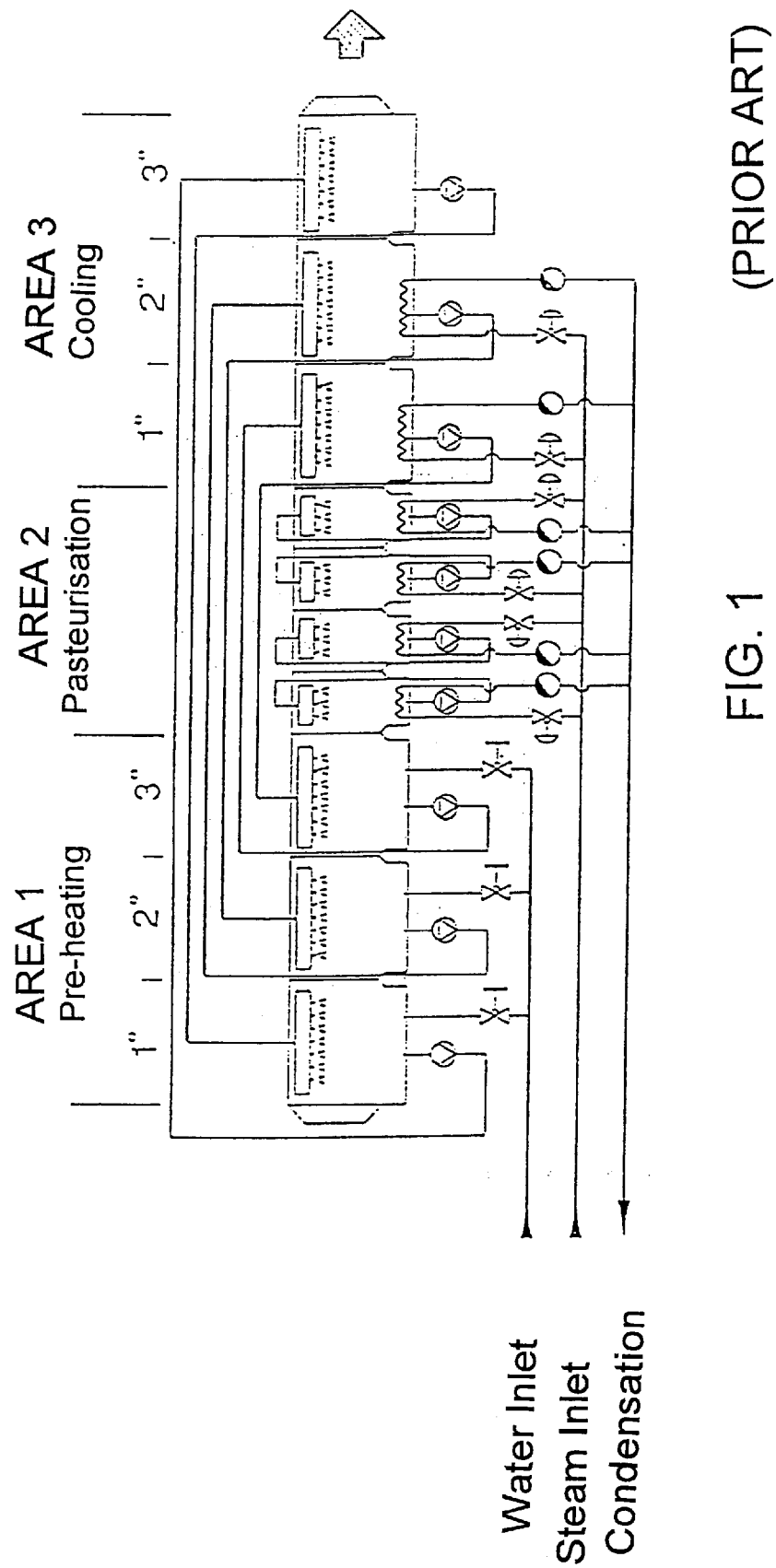
FIG. 1 shows a first example of prior art as previously described.
Figure 2:
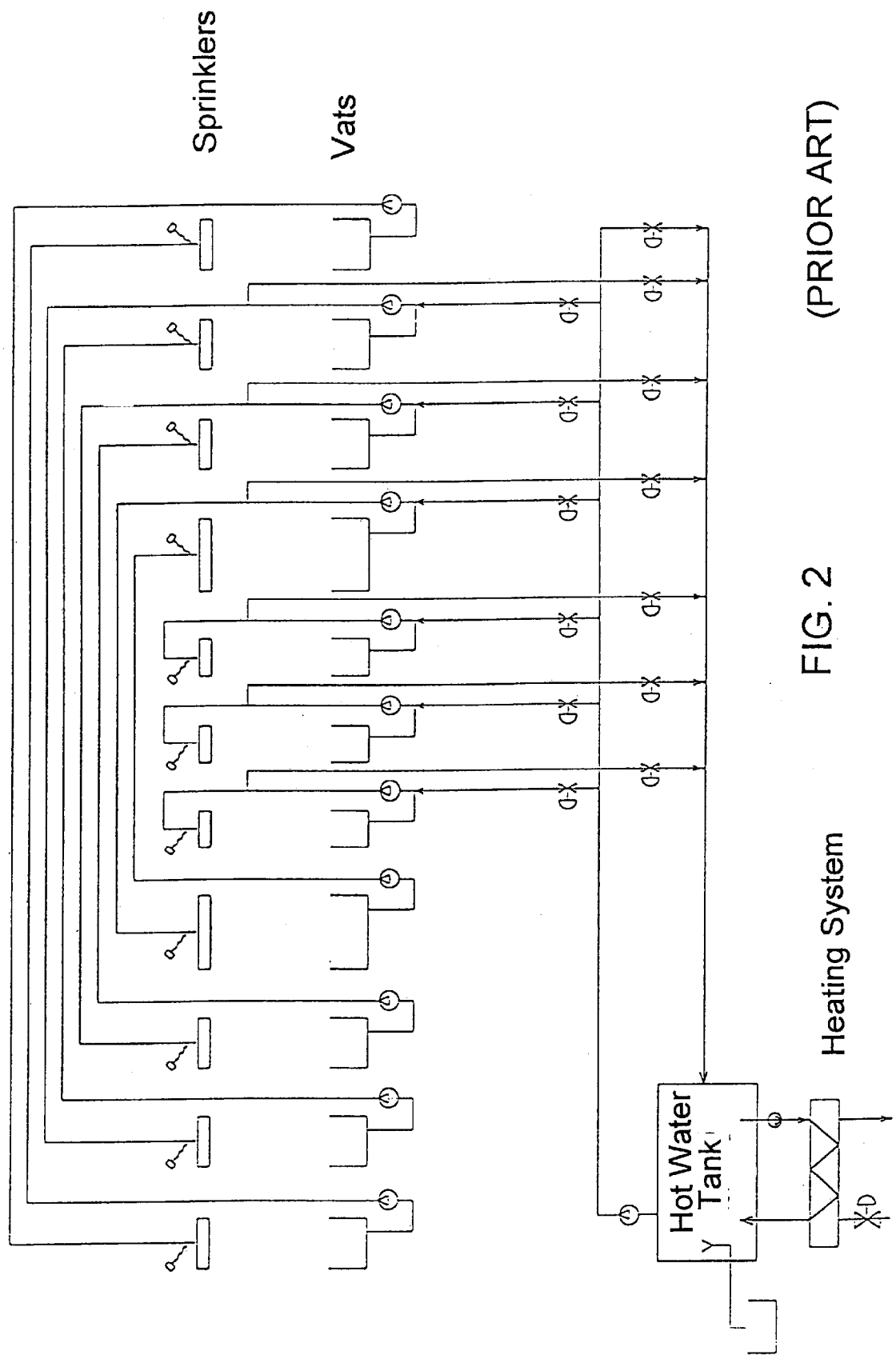
FIG. 2 shows a second example of prior art also as previously described.
Figure 3:
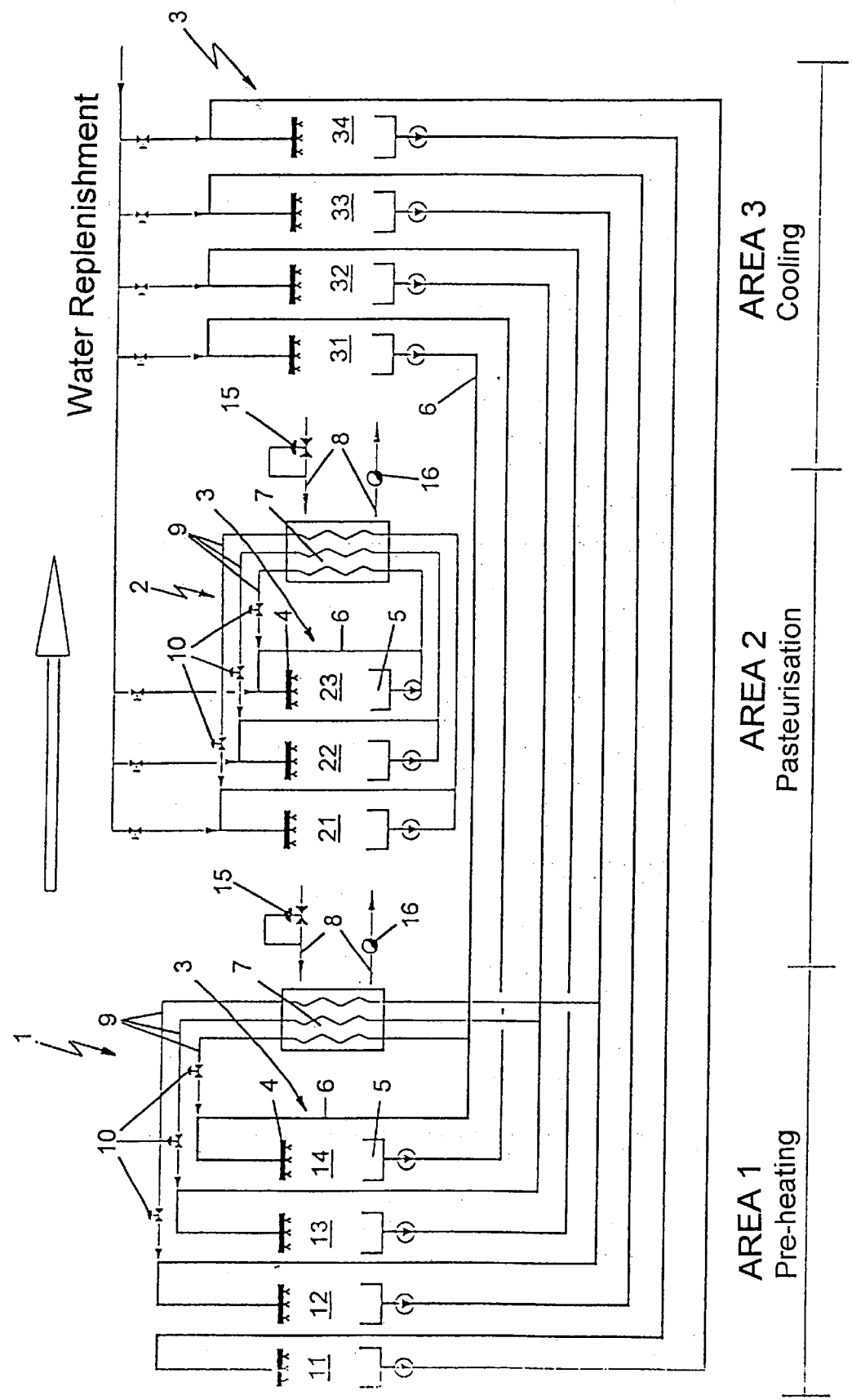
FIG. 3 schematically shows the hydraulic loops and the organs for heating and controlling the process temperatures relating to the apparatus of the present invention.

With reference to FIG. 3, the tunnel of the pasteurizer, which is provided with a conveyor (not shown) for advancing the product according to the direction indicated by the arrow shown in FIG. 3, is subdivided into three areas, i.e.: a first pre-heating area 1 which is subdivided (in the example shown) into four thermally independent elementary sub-areas 11, 12, 13, 14; a second area 2 for the pasteurizing heat treatment, which is subdivided (again with reference to the illustrated example) into three thermally independent sub-areas 21, 22, 23; a third cooling area 3 which is subdivided (also with reference to the illustrated example) into four elementary sub-areas 31, 32, 33, 34.

A suitable apparatus for measuring and processing data is able to measure and record process water temperature and to determine, by mathematical calculation, the temperature of the product in each of the elementary portions (sub-areas). Said apparatus is not shown in the accompanying drawings because it is known in itself (it is constituted by probes connected to a computer). Nor is its exact positioning shown (which in any case has to be in the areas or sub-areas of interest) because it depends on the various functional and operative requirements. Measured and recorded temperature values are constantly compared with set values (i.e. predetermined values) defined for a characteristic point of each of the elementary sub-areas of the areas 1, 2 and 3 into which the tunnel is subdivided. Such an apparatus for computerized adjustment and control is, in any case, described in patent EP 960 574.

Again with reference to FIG. 3, the apparatus for heating and controlling the process temperature shall now be described.

Each elementary sub-area of the pre-heating area 1 and of the area 2 for the pasteurizing heat treatment comprises a hydraulic loop 3 which allows to spray, with process water at predetermined temperature, the packaged product in transit on the conveyor.

With reference to the pasteurizing area 2, each hydraulic loop 3 in turn comprises a sprinkler 4, an underlying collection tank 5 and a pipeline 6 connecting the tank 5 with the sprinkler 4.

Note that, with reference to the pre-heating area 1, the pipeline 6 that connects the tank 5 with the sprinkler 4 extends its route to the cooling area 3. Starting from the tank 5, for instance of the sub-area 14, the pipeline 6 feeds the upper sprinkler of the sub-area 31 and hence the water drained from the tank of this sub-area 31 returns towards the sprinkler 4 of the sub-area 14. For the sake of descriptive simplicity the entire pipeline connecting the sub-areas 14 and 31 has been indicated with the same reference number 6 as the other similar pipelines.

Obviously, this holds true also for the other sub-areas 1, 12, 13 and 32, 33, 34.

According to the embodiment illustrated in FIG. 3, the apparatus of the present invention comprises two heat exchangers 7 associated respectively to the first pre-heating area 1 and to the second pasteurization heat treatment area 2.

Each exchanger 7 comprises a primary loop 8 (whereto are associated a metering valve 15 and a condensation drain 16) and a plurality of secondary loops 9 (as many as there are elementary sub-areas in which heated process water is present—this is not the case for sub-area 11). Each of the secondary loops is connected to the hydraulic loop 3 of each elementary sub-area.

More specifically, each loop 9 is fed in the lower part of the loop 3 by the process water coming from the tank 5 and ends in the upper part upstream of the sprinkler 4.

Each secondary circuit 9 is also provided with means for controlling the water temperature of the related sprinkler 4 which are constituted by a servo-controlled modulating low pressure valve 10 positioned, on the loop 9, upstream of the sprinkler 4.

The injection, or lack thereof, of process water (at a temperature deriving from the heat exchange in the exchanger 7) from the loop 9 to the hydraulic loop 3 determines the temperature variation of the water sprinkled by the sprinkler 4. This variation is a function of the water temperature in the circuit 9 downstream of the exchanger 7 and of the water flow rate injected downstream of the valve 10. Note that the use of loops 7 with multiple secondary loops 9 allows to maintain constantly active the system for adjusting the primary loop 8. And this thanks to the probability of energy demand by at least one of the secondary loops 9.

This fact allows:

both to reduce the inertia of regulating organs which from a state of inactivity were required suddenly to output maximum power, since it is likely that at least one of the elementary sub-areas served by the same exchanger 7 requires energy delivery at different times or at the same time;

and to have a good efficiency of the exchanger 7 and of the modulating valve 10 because their working range varies within contained values.

Note also that if in the primary loop 8 of the heat exchanger 7 the fluid were constituted by dry saturated steam, the assembly formed by metering valve 15 and condensation drain 16 would become self-regulating.

In this case the valve 15, the exchanger 7 and the condensation drain 16 would respectively become a pressure regulator 15 (the pressure of the dry saturated steam), a condenser 7 and a condensation drain 16. This means that, as long as in the secondary loops 9 circulates water that cools the steam present in the primary circuit 8 making it condense, the condensation drain 16 opens to make the condensation flow out in a quantity proportional to the heat exchanged and the pressure regulator (valve 15) opens to restore the value of pressure whereto it is calibrated. When the steam in the loop 8 is no longer cooled by any secondary fluid, no condensation being formed, the drain 16 closes, the pressure downstream of the pressure regulating valve 15 increases, and the valve itself shuts off the flow of steam.

Since the formation and evacuation of condensation is proportional to the heat removed from the water which may circulate in the secondary loops, the pressure variation of the steam in the condenser (heat exchanger 7) is proportional to the quantity of condensation evacuated, and the opening of the pressure regulating valve 15 is proportional to the pressure downstream thereof, the flow of steam in the primary loop 8 of the exchanger 7 is consequently regulated automatically as a function of the heat removed.

Obviously the present invention may assume, in its practical realization, different configurations from the one illustrated above, without thereby departing from the scope of protection of the present monopoly.

What is claimed is:

1. An apparatus for heating and controlling the process temperature in a tunnel pasteurizer, in particular for packaged food products, wherein the tunnel, provided with a conveyor able to advance the product, is substantially subdivided into a first pre-heating area, into a second pasteurization heat treatment area and into a third area where the product is cooled, said first, second and third area being considered each subdivided, in their length, into two or more thermally independent elementary sub-areas each of which comprising a hydraulic loop which allows to spray, with water at pre-set temperature, the packaged product, which hydraulic loop in turn comprises a sprinkler, and underlying collection tank and a pipeline connecting the collection tank with the sprinkler, said apparatus being provided at least with one heat exchanger comprising at least a primary loop and a plurality of secondary loops, each of said secondary loops being connected to said hydraulic loop of each said sub-area, each said secondary loop being provided with means for controlling the temperature of the water of the sprinkler comprised in said hydraulic loop of each sub-area.

2. An apparatus as claimed in claim 1, wherein said means for controlling the water temperature are constituted by servo-controlled low pressure modulating valves.

3. An apparatus as claimed in claim 1, wherein said first pre-heating area and said second pasteurization heat treatment area are each provided with said heat exchanger, the secondary loops of each said heat exchanger being connected to the corresponding hydraulic loops of said first pre-heating area and of said second pasteurization heat treatment area.

4. An apparatus as claimed in claim 1, wherein said pipeline, connecting the collection tank with the sprinkler in a sub-area of said first pre-heating area, collects the water of said collection tank and sends it to a sprinkler located in a sub-area of said third cooling area and, from the collection tank associated to the latter sprayer, returns it to the sprinkler of the sub-area of said first pre-heating area.

5. An apparatus as claimed in claim 1, wherein the fluid circulating in said primary loop of the heat exchanger is dry saturated steam.

* * * * *